US012042216B2

(12) United States Patent
Govari et al.

(10) Patent No.: US 12,042,216 B2
(45) Date of Patent: **\*Jul. 23, 2024**

(54) IRREVERSIBLE-ELECTROPORATION (IRE) BALLOON CATHETER WITH MEMBRANE-INSULATED HIGH-VOLTAGE BALLOON WIRES

(71) Applicant: BIOSENSE WEBSTER (ISRAEL) LTD., Yokneam (IL)

(72) Inventors: Assaf Govari, Haifa (IL); Andres Claudio Altmann, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 277 days.

This patent is subject to a terminal disclaimer.

(21) Appl. No.: 16/707,175

(22) Filed: Dec. 9, 2019

(65) Prior Publication Data

US 2021/0169567 A1  Jun. 10, 2021

(51) Int. Cl.
*A61B 18/14* (2006.01)
*A61M 25/10* (2013.01)
(Continued)

(52) U.S. Cl.
CPC ......... *A61B 18/1492* (2013.01); *A61M 25/10* (2013.01); *A61B 2018/0022* (2013.01);
(Continued)

(58) Field of Classification Search
CPC ........ A61B 18/1492; A61B 2018/0022; A61B 2018/00613; A61B 2090/3966
See application file for complete search history.

(56) References Cited

U.S. PATENT DOCUMENTS 4,709,698 A * 12/1987 Johnston ................ A61B 18/08
606/41
5,779,698 A * 7/1998 Clayman .............. A61B 18/082
607/101
(Continued)

FOREIGN PATENT DOCUMENTS

CN       107427321 A    12/2017
WO   WO2019055512 A1    3/2019

OTHER PUBLICATIONS

Vivek Y. Reddy, MD et al., "Pulsed Field Ablation for Pulmonary Vein Isolation in Atrial Fibrillation", Journal of the American College of Cardiology, vol. 74, No. 3, 2019.
(Continued)

*Primary Examiner* — Jaymi E Della

(57) ABSTRACT

A medical probe includes a shaft and an expandable balloon. The shaft is configured for insertion into an organ of a patient. The expandable balloon is coupled to a distal end of the shaft, with the expandable balloon including: (a) an expandable membrane having an outer surface and an inner surface, wherein the expandable membrane is configured to be expanded from a collapsed shape to a balloon shaped member, (b) a plurality of electrodes disposed on the outer surface of the expandable membrane, (c) one or more wires connected to the plurality of electrodes, the wires extending from the distal end to the electrode, (d) and an expandable cover that encapsulates the wires between the expandable cover and the expandable membrane so that the wires are constrained between the cover and the expandable membrane but the electrodes are exposed to ambient environment.

8 Claims, 3 Drawing Sheets

(51) Int. Cl.
 *A61B 18/00* (2006.01)
 *A61B 90/00* (2016.01)

(52) U.S. Cl.
 CPC ............... *A61B 2018/00613* (2013.01); *A61B 2090/3966* (2016.02); *A61M 2025/1043* (2013.01); *A61M 2210/125* (2013.01)

(56) References Cited

U.S. PATENT DOCUMENTS

| | | | |
|---|---|---|---|
| 8,048,067 B2 | 11/2011 | Davalos | |
| 8,221,411 B2 | 7/2012 | Francischelli | |
| 10,271,893 B2 | 4/2019 | Stewart | |
| 10,285,755 B2 | 5/2019 | Stewart | |
| 10,342,598 B2 | 7/2019 | Long | |
| 10,531,914 B2 | 1/2020 | Stewart | |
| 2008/0188912 A1* | 8/2008 | Stone | A61F 7/123 606/192 |
| 2012/0071870 A1* | 3/2012 | Salahieh | A61B 5/287 606/33 |
| 2015/0025532 A1* | 1/2015 | Hanson | A61B 18/1492 156/60 |
| 2015/0066013 A1 | 3/2015 | Salahieh | |
| 2015/0272652 A1* | 10/2015 | Ghaffari | A61B 18/20 600/561 |
| 2016/0051324 A1 | 2/2016 | Stewart | |
| 2017/0348049 A1* | 12/2017 | Vrba | A61B 18/1492 |
| 2017/0354463 A1 | 12/2017 | Mori | |
| 2019/0030328 A1 | 1/2019 | Stewart | |

OTHER PUBLICATIONS

Nebojsa Mujovic et al., "Catheter Ablation of Atrial Fibrillation: An Overview for Clinicians", Adv. Ther. 34: 1897-1917, 2017.
World Health Organization Study: Atrial Fibrillation is a Growing Global Health Concern, Dec. 17, 2013.
U.S. Appl. No. 62/769,424, filed Nov. 19, 2018.

* cited by examiner

IRREVERSIBLE-ELECTROPORATION (IRE) BALLOON CATHETER WITH MEMBRANE-INSULATED HIGH-VOLTAGE BALLOON WIRES

FIELD OF THE INVENTION

The present invention relates generally to the invasive medical probes, and particularly to balloon catheters for irreversible electroporation.

BACKGROUND OF THE INVENTION

Delivery of irreversible electroporation (IRE) energy to tissue was previously proposed in the patent literature. For example, U.S. Patent Application Publication 2019/0030328 describes a medical device configured to electroporate an area of tissue, the medical device including a balloon having a distal portion and a proximal portion, and a plurality of electrodes disposed on the distal portion of the balloon, each of the plurality of electrodes being configured to deliver electroporation energy to the area of tissue.

As another example, U.S. Pat. No. 10,285,755 describes a catheter having a distal expandable element coupled to the catheter body with a mesh or array of longitudinal splines substantially surrounding the expandable element, where at least a portion of the mesh or splines being electrically conductive. In an embodiment, an electrically insulated portion is disposed between two conductive portions of the mesh. The conductive portions may be operated in a bipolar manner to conduct current around the insulated portion and through tissue along pathways substantially parallel to a longitudinal axis of the expandable element between adjacent or otherwise spaced conductive portion of the mesh.

PCT International Publication WO 2019/055512 describes systems, devices, and methods for electroporation ablation therapy, including an endocardial ablation device that includes an inflatable member, such as a balloon, and at least one electrode for focal ablation by pulse delivery to tissue. In an embodiment, the ablation device includes a set of electrodes disposed on the balloon. The electrodes may be formed on a surface of a distal end of the balloon and be useful for forming lesions on endocardial surfaces via focal ablation. During use, the electrodes may be disposed in a chamber of the heart in order to deliver a pulse waveform to ablate tissue. The electrodes may each couple to a respective insulated electrical lead, with each lead having sufficient electrical insulation to sustain an electrical potential difference across its thickness without dielectric breakdown.

SUMMARY OF THE INVENTION

An exemplary embodiment of the present invention provides a medical probe including a shaft and an expandable balloon. The shaft is configured for insertion into an organ of a patient. The expandable balloon is coupled to a distal end of the shaft, with the expandable balloon including: (a) an expandable membrane having an outer surface and an inner surface, wherein the expandable membrane is configured to be expanded from a collapsed shape to a balloon shaped member, (b) a plurality of electrodes disposed on the outer surface of the expandable membrane, (c) one or more wires connected to the plurality of electrodes, the wires extending from the distal end to the electrode, (d) and an expandable cover that encapsulates the wires between the expandable cover and the expandable membrane so that the wires are constrained between the cover and the expandable membrane but the electrodes are exposed to ambient environment.

In some exemplary embodiments, the medical probe further includes a seal that runs over a distal edge of the cover membrane and is configured to seal the cover to the expandable membrane. In other exemplary embodiments, the seal covers a proximal edge of each of the electrodes.

In an exemplary embodiment, the electrodes are disposed equiangularly about a longitudinal axis of the expandable membrane. In another exemplary embodiment, each of the electrodes is coupled to the outer surface of the expandable membrane via a substrate.

In some exemplary embodiments, at least one of the electrodes includes a radiopaque marker having a configuration different from other radiopaque markers on the other electrodes.

In some exemplary embodiments, the plurality of electrodes is disposed over a distal hemisphere portion of the expendable membrane.

There is also provided, in accordance with an exemplary embodiment of the present invention, a method of manufacturing a medical probe, the method including assembling an expandable balloon by assembling an expandable membrane having an outer surface and an inner surface, wherein the expandable membrane is configured to be expanded from a collapsed shape to a balloon shaped member. A plurality of electrodes is disposed on the outer surface of the expandable membrane. Wires are connected to the plurality of electrodes, and using an expandable cover, the wires between the cover and the expandable membrane are encapsulated so that the wires are constrained between the cover and the expandable membrane but the electrodes are exposed to ambient environment. The expandable balloon is coupled to a distal end of a shaft.

In some exemplary embodiments, the method further includes sealing the cover against the expendable membrane using a seal running over a distal edge of the cover.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Figure 1:
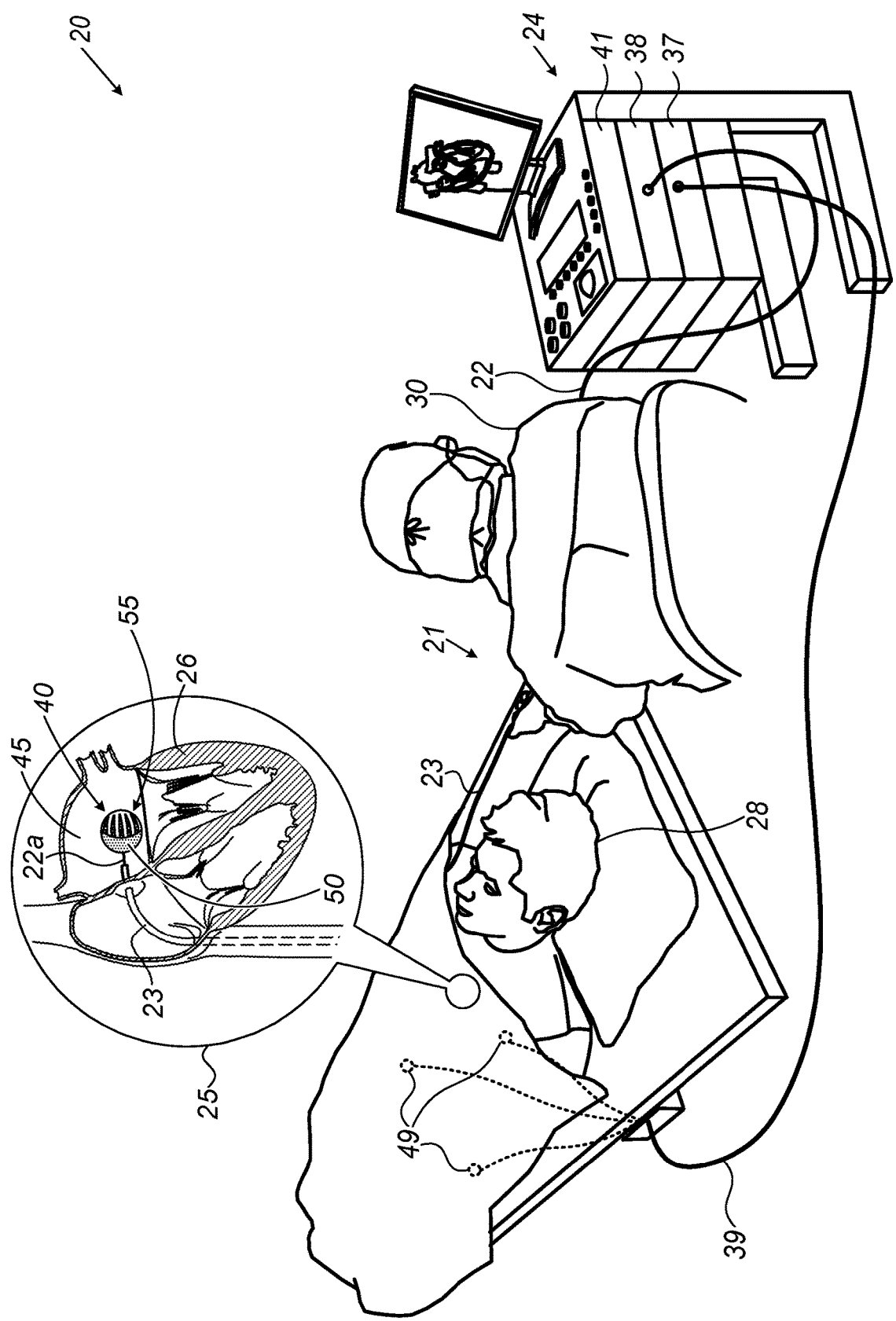
FIG. 1 is a schematic, pictorial illustration of a catheter-based irreversible electroporation (IRE) system, in accordance with an exemplary embodiment of the present invention.

Overview Irreversible electroporation (IRE), which is used as an invasive therapeutic modality, kills tissue cells by subjecting tissue to high-voltage pulses. A medical probe, such as a balloon catheter, may be used to apply high voltage pulses to tissue using a plurality of electrodes disposed on the balloon. For a wire used to conduct high voltage electrical signals to an electrode on the balloon, it would be detrimental to expose the wire to the ambient biological tissue environment (e.g., biological tissues or blood), as well as to the interior of the balloon. Therefore, the wiring to the balloon electrodes has to be sufficiently electrically insulated to prevent dielectric breakdown.

Exemplary embodiments of the present invention provide an IRE balloon catheter comprising insulated electrical wires. However, while the wires have their own insulation, this insulation may not be sufficient in an environment with high moisture content. Thus, the wires are disposed on an outer surface of an expandable membrane of the balloon catheter, so the wires are well separated from, for example, electrically conducting saline solution that is typically used for inflating the expandable membrane.

To achieve sufficient electrical insulation from the ambient environment, such as blood that is also electrically conducting, the wires are disposed between the expandable membrane and an encapsulating cover membrane, with the two membranes attached to each other in such a way that the wires are captured between the two membranes and only the electrodes connected to the wires are exposed to the ambient environment.

The disclosed IRE balloon catheter is coupled to a distal end of a hollow shaft for insertion into an organ of a patient. The expandable membrane is disposed about a longitudinal axis of the distal end of the shaft and is coupled at its distal end to an elongation rod. When pulled proximally into the hollow shaft, the elongation rod causes the expandable membrane to expand from an elongated, collapsed shape, to a balloon shaped member.

Each of the plurality of electrodes is connected to an output of an IRE pulse generator via one or more of the aforementioned wires disposed between the two membranes, where these highly insulated wires are coupled at a proximal end of the balloon catheter to supply wires that run inside the hollow shaft.

In some exemplary embodiments the cover membrane is sealed against the expendable membrane using a seal running over a distal edge of the cover membrane. Additionally or alternatively, the cover membrane is adhered to the outer surface of the expendable membrane, by, for example, gluing the cover membrane over its entire area to the outer surface of the expendable membrane.

The IRE balloon catheter is also configured to have the following features, which can be combined into various combinations or permutations, for example, each of the plurality of electrodes defining a shape optimized for IRE; each electrode disposed on the outer surface of the expandable membrane via a substrate; each electrode including a radiopaque marker having a configuration different from other radiopaque markers on the other electrodes; the expandable membrane including a generally spheroidal member and the expandable cover membrane including a hemi-spherical member.

The disclosed IRE balloon catheter enables application of IRE treatments in an electrically safe manner, and may thus improve the clinical outcome of invasive IRE treatments, such as of an IRE treatment of cardiac arrhythmia.

System Description

FIG. 1 is a schematic, pictorial illustration of a catheter-based irreversible electroporation (IRE) system 20, in accordance with an exemplary embodiment of the present invention. System 20 comprises a catheter 21, wherein a shaft 22 of the catheter is inserted into a heart 26 of a patient 28 through a sheath 23. The proximal end of catheter 21 is connected to a console 24.

Console 24 comprises an IRE generator 38 for applying IRE pulses via catheter 21 to irreversibly electroporate ostium tissue of a pulmonary vein in a left atrium 45 of the heart 26. In the exemplary embodiment described herein, catheter 21 may be used for any other suitable therapeutic and/or diagnostic purposes, such as electrical sensing and/or irreversibly electroporating other tissue of the heart 26.

A physician 30 inserts shaft 22 through the vascular system of patient 28. As seen in inset 25, an expandable balloon catheter 40 that is fitted at a distal end 22a of shaft 22 comprises a high-voltage insulation cover membrane 50 in a form of a hemisphere, further described in FIG. 2. During the insertion of shaft 22, balloon 40 is maintained in a collapsed configuration inside sheath 23. By containing balloon 40 in a collapsed configuration, sheath 23 also serves to minimize vascular trauma along the way to target location. Physician 30 navigates the distal end of shaft 22 to a target location in heart 26.

Once distal end 22a of shaft 22 has reached the target location, physician 30 retracts sheath 23, and expands balloon 40, among other means by pumping saline into an internal volume defined by the aforementioned expandable membrane. Physician 30 then manipulates shaft 22 to have electrodes 55 disposed on balloon catheter 40 engage an interior wall of the ostium, and operates console 24 to apply high-voltage IRE pulses via electrodes 55 to the ostium tissue.

Console 24 comprises a processor 41, typically a general-purpose computer, with suitable front end and interface circuits 37 for receiving signals from catheter 21 and from external-electrodes 49, which are typically placed around the chest of patient 26. For this purpose, processor 41 is connected to external-electrodes 49 by wires running through a cable 39.

Processor 41 is typically programmed (software) to carry out the functions described herein. The software may be downloaded to the computer in electronic form, over a network, for example, or it may, alternatively or additionally, be provided and/or stored on non-transitory tangible media, such as magnetic, optical, or electronic memory.

Although the illustrated exemplary embodiment relates specifically to the use of a balloon for IRE of heart tissue, the elements of system 20 and the methods described herein may alternatively be applied in controlling ablation using other sorts of multi-electrode ablation devices, such as multi-arm ablation catheters.

IRE Balloon Catheter with Membrane-Insulated High Voltage Balloon Wires

Figure 2:
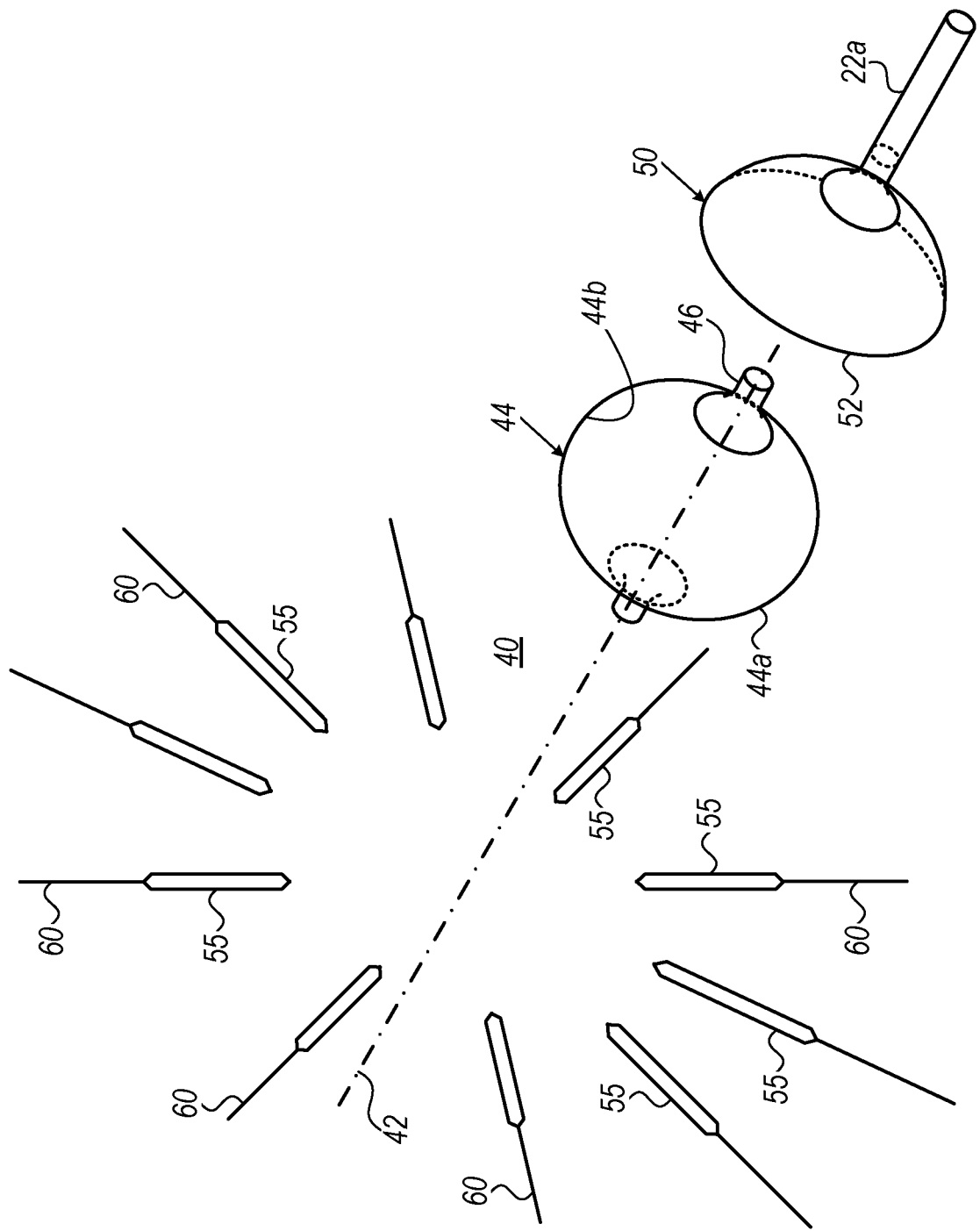
FIG. 2 is an exploded perspective view of the irreversible electroporation (IRE) balloon catheter of FIG. 1, in accordance with an exemplary embodiment of the present invention.

FIG. 2 is an exploded perspective view of irreversible electroporation (IRE) balloon catheter 40 of FIG. 1, in accordance with an exemplary embodiment of the present invention.

An expandable membrane 44 of balloon catheter 40 is attached to distal end 22a of shaft 22 at a proximal membrane portion 46 of membrane 44. Membrane 44 is disposed about a longitudinal axis 42 and has an outer surface 44a and an inner surface 44b. Outer surface 44a is exposed to the ambient environment while inner surface 44b is exposed to an internal volume of the balloon defined by membrane 44.

Expandable membrane 44 is configured to be expanded from a collapsed shape (generally an elongated tubular configuration) to a balloon (or generally spheroidal) shaped member. A plurality of electrodes 55 are disposed on outer surface 44a of the expandable membrane 44. Electrodes 55 are arranged equidistantly over a distal hemisphere portion of membrane 44. In the illustrated exemplary embodiment, each of electrodes 55 is connected to an insulated electrical wire 60, which is electrically connected to conduct high voltage to the electrode. Each wire 60 comprises an electrically conductive core surrounded by an electrically insulating sleeve. Electrical wires 60 are coupled to the output of IRE generator 24 by wiring (not shown) that run via hollow shaft 22 to console 24.

The underside surface of each electrode 55 is the electrode surface that is not exposed to the ambient environment and is typically bonded to outer surface 44a of membrane 44.

An expandable cover membrane 50, having a border 52, encapsulates wires 60 between cover membrane 50 and expandable membrane 44 so that wires 60 are constrained between membrane 44 and cover membrane 50. Expandable cover membrane 50 is also referred to herein simply as "cover, "cover membrane" or "expandable cover," for brevity and for avoiding confusion with membrane 44. In this way, wires 60 are resilient to dielectric breakdown due to high voltage electrical signals that they conduct during an IRE procedure. In other words, the total electrical insulation between the cores of wires 60 and the ambient environment comprises both the insulation of the insulating sleeves of wires 60, and the insulation of cover membrane 50. In an exemplary embodiment, cover membrane 50 is secured to the expandable balloon with an adhesive (not shown).

Figure 3:
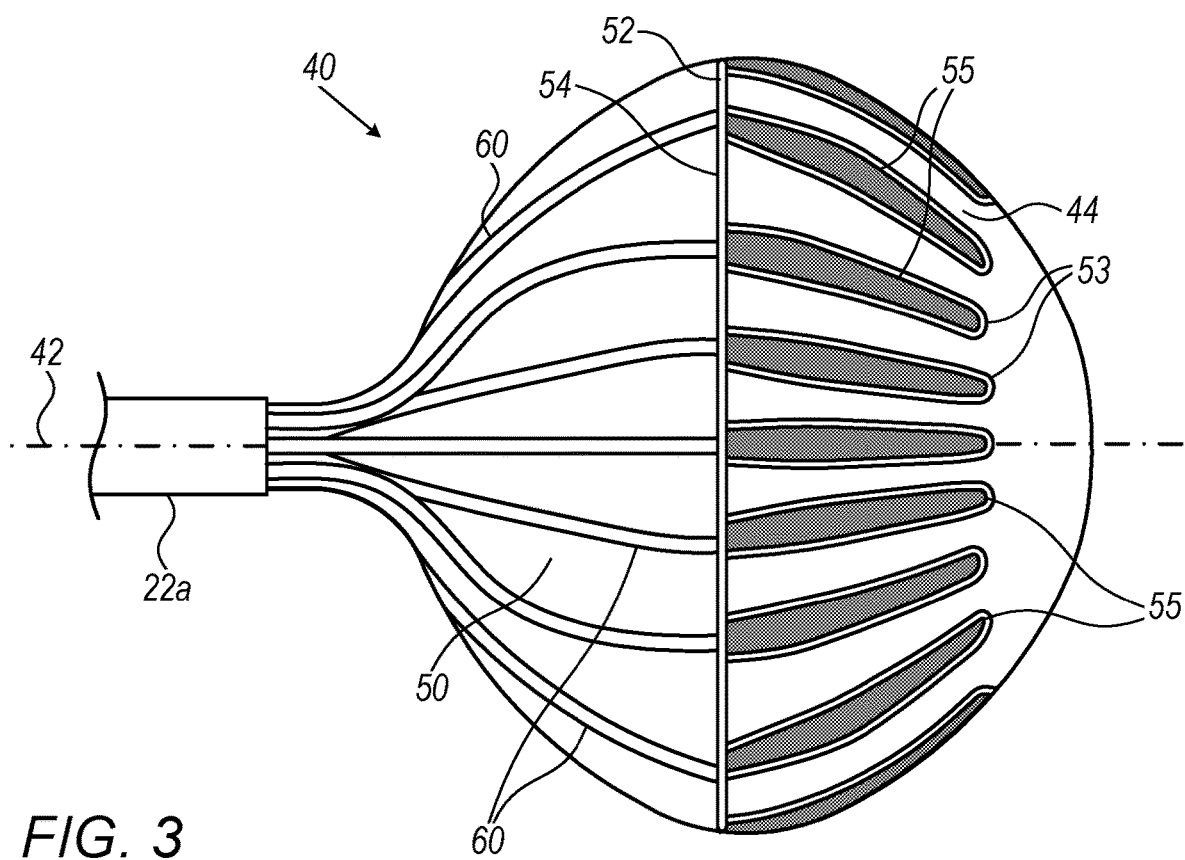
FIG. 3 is a side view of the assembled irreversible electroporation (IRE) balloon catheter of FIG. 2, in accordance with an exemplary embodiment of the present invention.

FIG. 3 is a side view of the assembled irreversible electroporation (IRE) balloon catheter 40 of FIG. 2, in accordance with an exemplary embodiment of the present invention. As seen, each of the plurality of electrodes 55 defines an area not covered by expandable cover membrane 50 to allow the electrodes to be exposed to the ambient environment.

The plurality of electrodes 55 is disposed equiangularly about longitudinal axis 42 such that cover membrane 50 encapsulates a proximal edge of each electrode 55. A seal 54 runs over border 52 (i.e., over the proximal edge of electrodes 55) of cover membrane 50 and may extend by up to few millimeters over a proximal portion of the outer surface of electrodes 55 while allowing the electrodes to be exposed to the ambient environment. In an embodiment, seal 54 can be provided in a form of a polyurethane or epoxy seal.

Typically, each electrode 55 is coupled to the outer surface of expandable membrane 44 via a substrate 53 which itself is connected, or bonded, to the outer surface of membrane 44.

As can be seen in FIG. 3, each wire 60 on membrane 44 extends from distal end 22a to a respective electrode 55 such that each wire follows the topographic outer surface of membrane 44.

As each wire 60 may be used to conduct high voltage electrical signals, it would be detrimental to expose wires to the ambient biological tissue environment (e.g., biological tissues or blood). While each wire 60 has its own insulating sleeve, this insulation may not be sufficient in a high humidity environment, especially in view of the high voltages involved. As such, expandable cover membrane 50 eliminates potential electrical breakdown between a wire and the ambient environment. The electrodes remain exposed to biological tissue so that the electrodes can perform their intended purposes. Moreover, as wires 60 are constrained or captured between the two membranes, there is virtually no likelihood of the wires being entangled or mis-connected to the wrong electrode during assembly.

The exterior wall of membranes 44 and 50 is typically made of a bio-compatible material, for example, formed from a plastic (e.g., polymer) such as polyethylene terephthalate (PET), polyurethane or PEBAX®. These plastics provide sufficient electrical insulation against dielectric breakdown under the strong electric fields occurring with IRE pulses.

Any of the examples or exemplary embodiments described herein may include various other features in addition to or in lieu of those described above. In particular, the exemplary configurations shown in FIGS. 2 and 3 are chosen purely for the sake of conceptual clarity. For example, cover membrane 50 may be glued over its internal surface to the outer surface of the expendable membrane 44.

Although the exemplary embodiments described herein mainly address IRE procedures, the disclosed techniques can be used for other suitable applications, such as for electrophysiological (EP) sensing. Examples of EP catheters are described, for example, in U.S. Provisional Patent Application 62/769,424, filed Nov. 19, 2018, which is assigned to the assignee of the present patent application and whose disclosure is incorporated herein by reference.

Although the exemplary embodiments described herein mainly address cardiac applications, the methods and systems described herein can also be used in other medical applications, such as in neurology, otolaryngology, and general surgical procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical probe for irreversible electroporation, the medical probe comprising:
   a shaft for insertion into an organ of a patient; and
   an expandable balloon coupled to a distal end of the shaft, the expandable balloon comprising:
      an expandable membrane having an outer surface and an inner surface, wherein the expandable membrane is configured to be expanded from a collapsed shape to a balloon shaped member;
      a plurality of electrodes disposed on the outer surface of the expandable membrane, wherein each of the plurality of electrodes are disposed at a same longitudinal distance from the distal end of the shaft;
      one or more first wires connected to each of the plurality of electrodes, the one or more first wires extending from the distal end to the plurality of electrodes, wherein each of the one or more first wires is insulated in a sleeve and follows a contour of the expandable member;
      one or more second wires running through a hollow in the shaft, wherein the one or more first wires are coupled at a proximal end of the expandable balloon to the one or more second wires, wherein the one or more second wires are other than the one or more first wires; and an expandable cover that encapsulates the one or more first wires between the expandable cover and the expandable membrane so that the one or more first wires are constrained between the expandable cover and the expandable membrane but the plurality of electrodes are exposed to ambient environment, the expandable cover extends over a portion of the plurality of electrodes and is adhered to the expandable member, wherein a distal edge of the expandable cover is a circle that extends around a perimeter of the expandable balloon and overlaps a proximal portion of each of the plurality of electrodes;

a seal that runs over the distal edge of the expandable cover and is configured to seal the expandable cover to the expandable membrane wherein the seal directly covers a proximal edge of each of the plurality of electrodes; and wherein the distal edge of the expandable cover overlaps only the proximal portion of each of the plurality of electrodes and the seal directly covers only the proximal edge of each of the plurality of electrodes.

2. The medical probe according to claim 1, wherein the plurality of electrodes are disposed equiangularly about a longitudinal axis of the expandable membrane.

3. The medical probe according to claim 1, wherein each of the plurality of electrodes is coupled to the outer surface of the expandable membrane via a substrate.

4. The medical probe according to claim 1, wherein at least one of the plurality of electrodes comprises a radiopaque marker having a configuration different from other radiopaque markers on others of the plurality of electrodes.

5. The medical probe according to claim 1, wherein the plurality of electrodes is disposed over a distal hemisphere portion of the expandable membrane.

6. A method of manufacturing a medical probe for irreversible electroporation, the method comprising:
assembling an expandable balloon by:
assembling an expandable membrane having an outer surface and an inner surface, wherein the expandable membrane is configured to be expanded from a collapsed shape to a balloon shaped member;

disposing a plurality of electrodes on the outer surface of the expandable membrane;

connecting one or more first wires to each of the plurality of electrodes, wherein the one or more first wires are each insulated in a sleeve and follow a contour of the expandable membrane;

coupling one or more second wires to the one or more first wires at a proximal end of the expandable balloon, wherein the one or more second wires run through a hollow in the shaft; and using an expandable cover, encapsulating the one or more first wires between the expandable cover and the expandable membrane so that the one or more first wires are constrained between the expandable cover and the expandable membrane but the plurality of electrodes are exposed to ambient environment, and wherein the expandable cover extends over a portion of the plurality electrodes and is adhered to the expandable member, wherein a distal edge of the expandable cover is a circle that extends around a perimeter of the expandable balloon and overlaps a proximal portion of each of the plurality of electrodes;

coupling the expandable balloon to a distal end of a shaft;

sealing the expandable cover against the expandable membrane using a seal running over a distal edge of the expandable cover, wherein the expandable membrane is spherical in its expanded configuration and wherein the seal directly covers a proximal edge of each of the plurality of electrodes; and wherein the distal edge of the expandable cover overlaps only the proximal portion of each of the plurality of electrodes and the seal directly covers only the proximal edge of each of the plurality of electrodes.

7. The medical probe according to claim 1, wherein the one or more first wires are more highly insulated as compared to the one or more second wires.

8. The method according to claim 6, wherein the one or more first wires are more highly insulated as compared to the one or more second wires.

* * * * *